United States Patent
Lee et al.

(10) Patent No.: US 9,753,004 B2
(45) Date of Patent: Sep. 5, 2017

(54) ELECTROCHEMICAL BIOSENSOR WITH IMPROVED ACCURACY

(71) Applicant: I-SENS, INC., Seoul (KR)

(72) Inventors: Myeong Ho Lee, Seoul (KR); Moon Hwan Kim, Seoul (KR); Ung Ki Lee, Incheon (KR); Han Be Park, Gangwon-do (KR); Sung-Kwon Jung, Incheon (KR); Hakhyun Nam, Seoul (KR); Geun Sig Cha, Seoul (KR)

(73) Assignee: I-Sens, Inc., Seoul (KR)

( * ) Notice: Subject to any disclaimer, the term of this patent is extended or adjusted under 35 U.S.C. 154(b) by 72 days.

(21) Appl. No.: 14/556,891

(22) Filed: Dec. 1, 2014

(65) Prior Publication Data

US 2015/0083613 A1    Mar. 26, 2015

Related U.S. Application Data

(63) Continuation of application No. PCT/KR2013/004838, filed on May 31, 2013.

(30) Foreign Application Priority Data

Jun. 1, 2012    (KR) .................... 10-2012-0059327

(51) Int. Cl.
*G01N 27/327* (2006.01)
*G01N 33/66* (2006.01)
*C12Q 1/00* (2006.01)

(52) U.S. Cl.
CPC ......... *G01N 27/3277* (2013.01); *C12Q 1/006* (2013.01); *G01N 27/3272* (2013.01); *G01N 27/3274* (2013.01); *G01N 33/66* (2013.01)

(58) Field of Classification Search
None
See application file for complete search history.

(56) References Cited

U.S. PATENT DOCUMENTS

| | | | |
|---|---|---|---|
| 4,301,412 A | 11/1981 | Hill et al. | |
| 5,658,444 A | 8/1997 | Black et al. | |
| | (Continued) | | |

FOREIGN PATENT DOCUMENTS

| | | |
|---|---|---|
| EP | 2 741 064 | 6/2014 |
| JP | 2000338076 | 12/2000 |
| | (Continued) | |

OTHER PUBLICATIONS

"Adhesives Research" (created Apr. 14, 2012, accessed Apr. 8, 2016).*

(Continued)

*Primary Examiner* — Luan Van
*Assistant Examiner* — Steven E Rosenwald
(74) *Attorney, Agent, or Firm* — Lathrop & Gage LLP

(57) ABSTRACT

The present invention relates to an electrochemical biosensor with improved hematocrit measurement accuracy for measuring blood glucose. According to the present invention, an electrochemical biosensor including a first electrode part for correcting a measured hematocrit value and a second electrode part for measuring a glucose concentration is effective in improving accuracy of a measured hematocrit value and in more improving accuracy of a measured blood glucose concentration using the measured hematocrit values for correction, because an insulation cover is made thinner than a working electrode and an auxiliary electrode, so that areas of a first working electrode and a first auxiliary electrode of the first electrode part exposed to a blood sample become equal; a distance between the first working electrode and the second working electrode becomes constant; and electrode areas are maintained constantly by the insulation cover even when a positioning error occurs during printing.

14 Claims, 10 Drawing Sheets

(56) References Cited

U.S. PATENT DOCUMENTS

| | | | |
|---|---|---|---|
| 6,241,862 B1 | 6/2001 | McAleer et al. | |
| 6,287,451 B1 | 9/2001 | Winarta et al. | |
| 6,837,976 B2 * | 1/2005 | Cai | G01N 27/3272 204/403.03 |
| 7,452,457 B2 * | 11/2008 | Burke | G01N 27/3274 205/775 |
| 7,611,621 B2 * | 11/2009 | Cai | A61B 5/14546 204/403.01 |
| 2005/0023152 A1 * | 2/2005 | Surridge | C12Q 1/001 205/775 |
| 2009/0056120 A1 | 3/2009 | Bhullar et al. | |
| 2010/0219084 A1 | 9/2010 | Blythe et al. | |
| 2011/0139634 A1 * | 6/2011 | Chou | G01N 27/3274 205/792 |

FOREIGN PATENT DOCUMENTS

| | | |
|---|---|---|
| KR | 100586832 | 6/2006 |
| WO | 01/57510 | 8/2001 |
| WO | 2004/038401 | 5/2004 |

OTHER PUBLICATIONS

International Search Report for international application No. PCT/KR2013/004838, mailed Aug. 19, 2013.

* cited by examiner

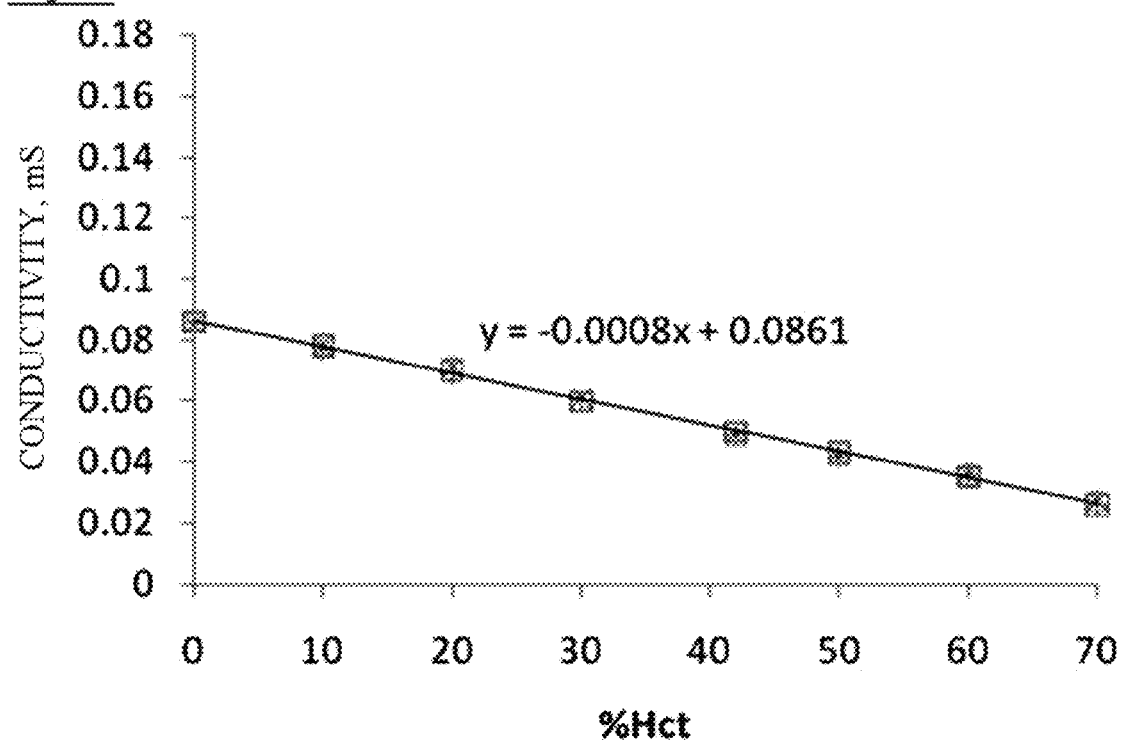

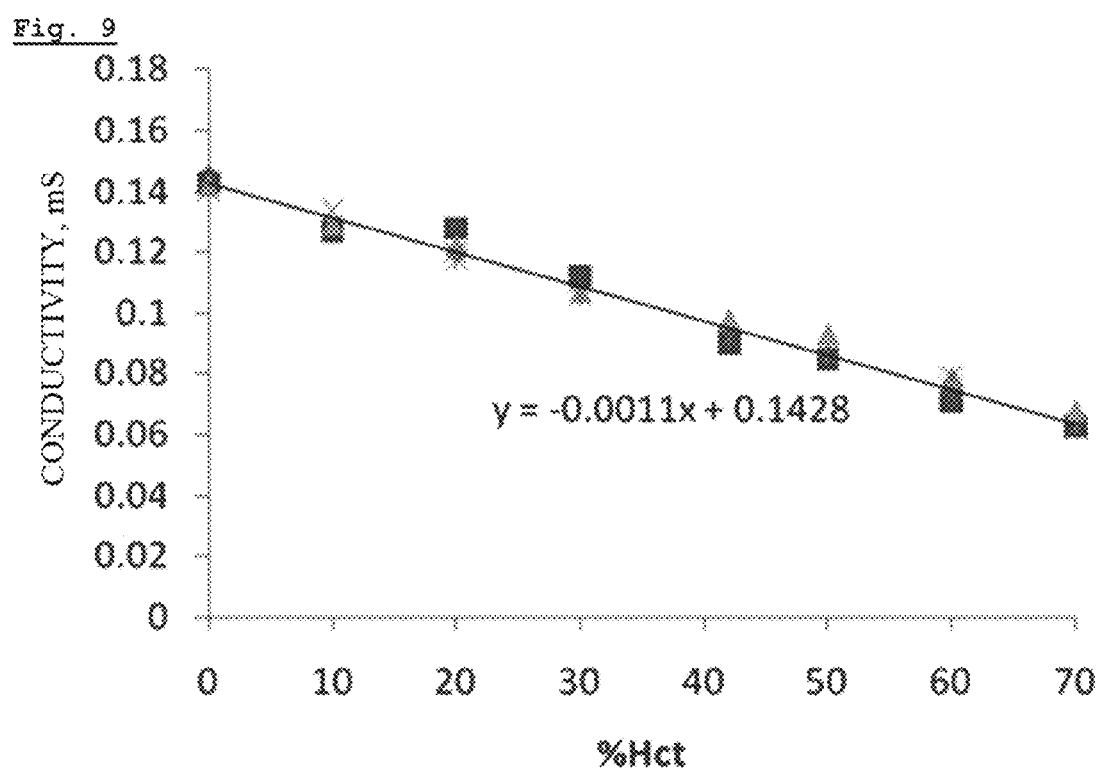

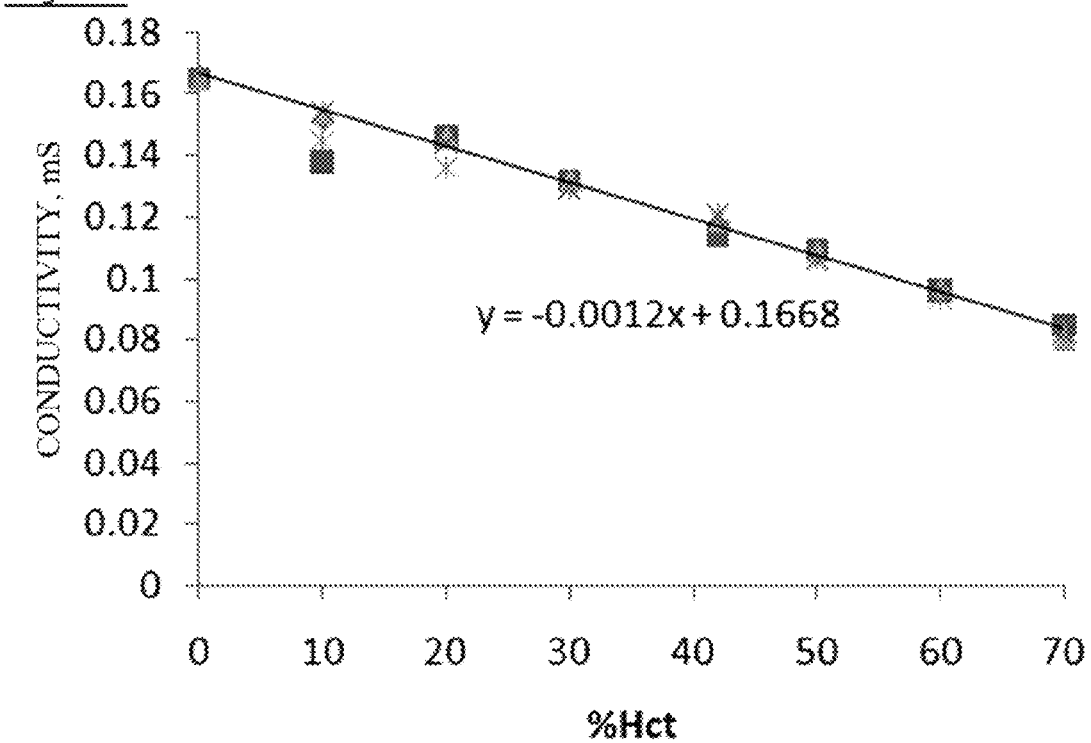

ELECTROCHEMICAL BIOSENSOR WITH IMPROVED ACCURACY

TECHNICAL FIELD

The present invention relates to a biosensor with improved measurement accuracy by imparting, to an electrochemical biosensor, a function of correcting influence of blood sample properties, particularly hematocrit.

BACKGROUND ART

Recently, there has been increased need for periodically measuring the glucose level in blood (i.e., blood glucose) to diagnose and prevent diabetes. The blood glucose may be easily measured by using a hand-held and portable measuring device. Specifically, individual patients may easily measure blood glucose by using a biosensor in a strip form. Such a biosensor for measuring blood glucose is based on a colorimetric method or an electrochemical method as working principles.

Among these, the electrochemical method is explained by following Reaction Formula I and primarily characterized by using an electron transfer mediator. Examples of the electron transfer mediator may include ferrocene, and ferrocene derivatives; quinone, and quinine derivatives; organic and inorganic materials containing transition metals (e.g., hexamine ruthenium, osmium-containing polymers, potassium ferricyanide, etc.); and electron transfer organic materials such as organic conductive salts and viologen.

[Reaction Formula 1]

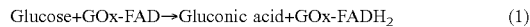
(1)

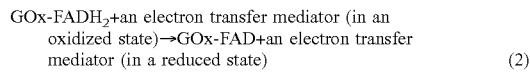
(2)

(In Reaction Formula 1, GOx indicates glucose oxidase; and GOx-FAD and GOx-FADH$_2$ respectively indicate an oxidized state and a reduced state of flavin adenine dinucleotide (FAD) which is an active site of glucose oxidase.)

As shown in Reaction Formula 1, glucose in blood is firstly oxidized into gluconic acid by catalysis of glucose oxidase (1). In this step, FAD, which is an active site of glucose oxidase, is reduced to FADH$_2$. Then, the reduced FADH$_2$ is oxidized to FAD through a redox reaction with an electron transfer mediator and renders the electron transfer mediator reduced (2). The obtained electron transfer mediator in a reduced state can spread to a surface of an electrode. Then, the blood glucose concentration is determined by measuring electric current generated when an oxidation potential of the electron transfer mediator in a reduced state is applied to a surface of a working electrode.

Sometimes, if there is a need for reducing influence of oxygen in a blood sample, glucose dehydrogenase such as GDH-FAD is used in replacement of glucose oxidase GOx-FAD. Even though the types of enzymes are varied, the overall reaction follows the process in Reaction Formula 1.

A biosensor employing the above-mentioned electrochemical method as working principles is referred to as an electrochemical biosensor. In contrast to a biosensor using the conventional colorimetric method, the electrochemical biosensor is advantageous in that: influence of oxygen can be reduced; and a sample can be used without separate pretreatment even in the case where the sample is turbid.

Generally, although the electrochemical biosensor is conveniently used to monitor and control the blood glucose level, accuracy of the sensor is largely affected by various interfering species such as uric acid, acetaminophene, and ascorbic acid susceptible to oxidation.

Further, as a factor of causing a severe error in measurement accuracy of the electrochemical biosensor, erythrocyte volume fraction (i.e., a volumetric ratio of red blood cells in the whole blood; hematocrit) serves a key role. For people who regularly measure their blood glucose level by using a disposable biosensor strip, a biosensor, which is largely affected by hematocrit level, may bring about misjudgment in the measured result, and therefore cause even danger to lives of users.

Thus, hematocrit measurement accuracy is very important, since accuracy of the electrochemical biosensor in sensing hematocrit directly affects measurement accuracy of the blood glucose concentration eventually.

Patent documents 1 and 2 disclose a method for separating red blood cells, or a method for applying, to a reagent layer, a layer which eliminates red blood cells.

Patent document 3 discloses a method for using a screen-printable sensitive layer which includes silica filler and has an integrated function of reagent/blood cell separation.

Patent document 4 discloses a correction method of mathematically treating, through a chemometirc method, results obtained by applying an applied potential twice (i.e., the double excitation potential).

Measurement accuracy may be increased by providing an electrode for directly measuring hematocrit through electrical conductivity or resistance separately from an electrode for measuring an enzymatic reaction to separately measure hematocrit, and by using these results to correct a glucose concentration obtained from the enzymatic reaction measuring electrode. It has been suggested, as a prior art, a method capable of measuring hematocrit through conductivity of a disposable sensor equipped with an auxiliary electrode and a working electrode mounted on a sample cell in a capillary tube type (see Patent document 5), and also there is an example of applying this method to a biosensor for blood glucose measurement (see Patent document 6).

The present invention is focused on manufacturing of a sensor for accurately measuring conductivity in mass production of the sensor. Blood electrical conductivity (G) is based on Equation (1) below.

$$G = \sigma A / L \quad (1)$$

In Equation (1), G indicates electrical conductivity expressed in $\Omega^{-1}$ unit; $\sigma$ indicates a conductivity coefficient of blood expressed in $\Omega^{-1}$ cm$^{-1}$ unit; A indicates an area of an electrode expressed in cm$^2$ unit; and L indicates a distance between electrodes expressed in cm unit. Accordingly, a constant distance between electrodes and constant area of the electrode are important for accurately measuring conductivity.

However, the prior art technique never discloses how to control the distance between electrodes and the area of the conductivity measuring electrode for measuring hematocrit to be constant in a mass-production type biosensor.

In the electrochemical biosensor, electrodes are formed by a printing method in most cases. However, during printing electrodes, deviations in a distance between electrodes and an area of the electrode are likely to occur, since printing is not carried out as exactly as desired depending on constituent materials, and an inclined edge of the electrode tends to slightly flow down. Also, as the printed electrode is getting thicker, a reaction occurred at the inclined edge has a greater effect on overall measurement. There is another problem in that, when even a small error occurs during electrode printing, areas of a working electrode and an auxiliary electrode are greatly varied. Such non-uniformity in electrode areas tends to be much severer in an electrode for measuring conductivity directly using an alternating current than in an electrode for an enzymatic reaction, thereby leading to a decrease in accuracy and precision of blood glucose measurement using hematocrit as a correction factor.

Therefore, while studying an electrochemical biosensor with more improved hematocrit measurement accuracy, the present inventors have completed the present invention by finding that, in an electrochemical biosensor including a first electrode part for correcting a measured value of hematocrit and a second electrode part for measuring a blood glucose concentration, an insulation cover is made thinner than a working electrode and an auxiliary electrode, so that areas of a first working electrode and a first auxiliary electrode of the first electrode part exposed to a blood sample become equal and electrode areas are maintained constantly by the insulation cover even when a positioning error occurs during printing.

Patent document 1: JP 2000338076 A
Patent document 2: U.S. Pat. No. 5,658,444 A1
Patent document 3: U.S. Pat. No. 6,241,862 B1
Patent document 4: WO 01/57510 A2
Patent document 5: U.S. Pat. No. 4,301,412 A1
Patent document 6: US 20110139634 A1.

DISCLOSURE OF THE INVENTION

Technical Problem

One object of the present invention is to provide an electrochemical biosensor for measuring blood glucose with improved accuracy in hematocrit measurement.

Another object of the present invention is to provide a method for precisely measuring a blood glucose concentration by assaying a hematocrit value using the biosensor.

Technical Solution

In order to achieve the objects, the present invention provides an electrochemical biosensor, comprising:
  a lower substrate;
  a first electrode part including a first working electrode and a first auxiliary electrode which are formed on the lower substrate;
  a second electrode part including a second working electrode and a second auxiliary electrode which are formed on the lower substrate;
  a reagent layer formed on the second working electrode or the second auxiliary electrode, the reagent layer including an electron transfer mediator;
  an insulation cover having regions which correspond to first, second and third reaction units and are partitioned to have cavities, respectively, wherein the first reaction unit is positioned at the first working electrode, a second reaction unit is positioned at the first auxiliary electrode, and a third reaction unit is positioned at the second working electrode;
  an intermediate substrate equipped with a microchannel sample cell part to successively guide a blood sample into the first electrode part and the second electrode part; and
  an upper substrate,
  wherein areas of and a distance between the first working electrode and the first auxiliary electrode exposed at the first reaction unit and the second reaction unit are constant by means of the insulation cover.

Furthermore, the present invention provides a method for precisely measuring a blood glucose concentration by applying a hematocrit value using the biosensor, the method comprising:
  introducing a blood sample into a microchannel sample cell part (step 1);
  calculating a hematocrit value by measuring an electrical conductivity of the blood sample at a first electrode part (step 2);
  calculating a glucose concentration by measuring a signal at a second electrode part (step 3); and
  correcting the glucose concentration calculated at the second electrode part by applying the hematocrit value calculated at the first electrode part (step 4).

Advantageous Effects

According to the present invention, an electrochemical biosensor including a first electrode part for correcting a measured hematocrit value and a second electrode part for measuring a glucose concentration is effective in improving accuracy of a measured hematocrit value and in more improving accuracy of a measured blood glucose concentration using the measured hematocrit values for correction, because an insulation cover is made thinner than a working electrode and an auxiliary electrode, so that areas of a first working electrode and a first auxiliary electrode of the first electrode part exposed to a blood sample become equal; a distance between the first working electrode and the first auxiliary electrode becomes constant; and electrode areas are maintained constantly by the insulation cover even when a positioning error occurs during printing.

BRIEF DESCRIPTION OF THE DRAWINGS

FIG. 8 is a graph showing measured results of electrical conductivity versus hematocrit by using the sensor produced in Example 1 (where, "% Hct" means % hematocrit).

FIG. 9 is a graph showing measured results of electrical conductivity versus hematocrit by using the sensor produced in Comparative Example 1 (where, "% Hct" means % hematocrit).

FIG. 10 is a graph showing measured results of electrical conductivity versus hematocrit by using the sensor produced in Comparative Example 2 (where, "% Hct" means % hematocrit).

EXPLANATION FOR REFERENCE NUMERALS

Figure 1:
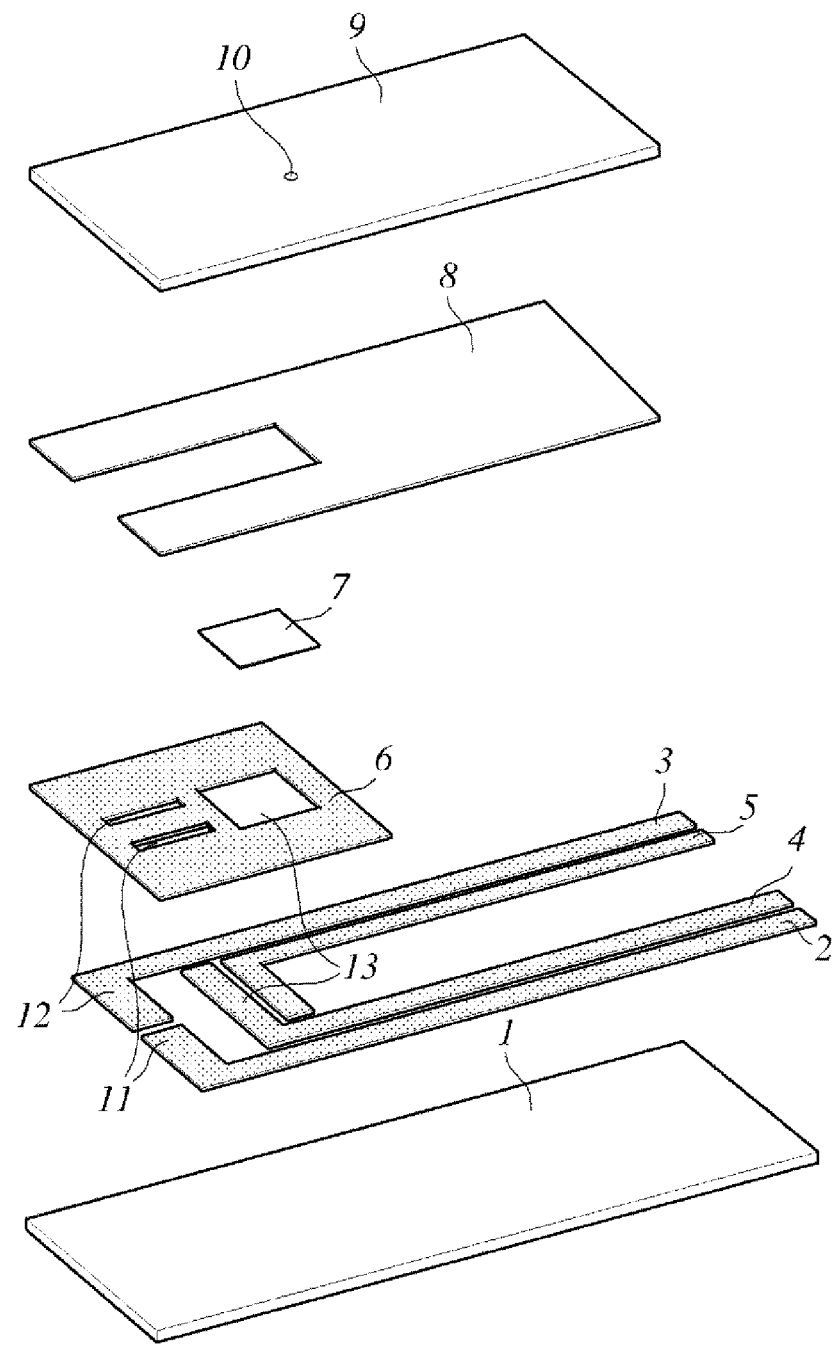
FIG. 1 is an exploded perspective view of a planar electrochemical biosensor, wherein the electrochemical biosensor according to Example 1 of the present invention has a first working electrode and a first auxiliary electrode, which are exposed to a blood sample, positioned perpendicular to a blood inflow direction and areas of the electrodes and a distance between the electrodes are maintained constantly by means of an insulation cover 6.

1: Lower substrate
2: First working electrode
3: First auxiliary electrode
4: Second working electrode
5: Second auxiliary electrode
6: Insulation cover
7: Reagent layer
8: Intermediate layer
9: Upper substrate
10: Air outlet
11: First reaction unit
12: Second reaction unit
13: Third reaction unit
14: Measuring Device

BEST MODE FOR CARRYING OUT THE INVENTION

Hereinafter, the present invention will be described in more detail.

Figure 2:
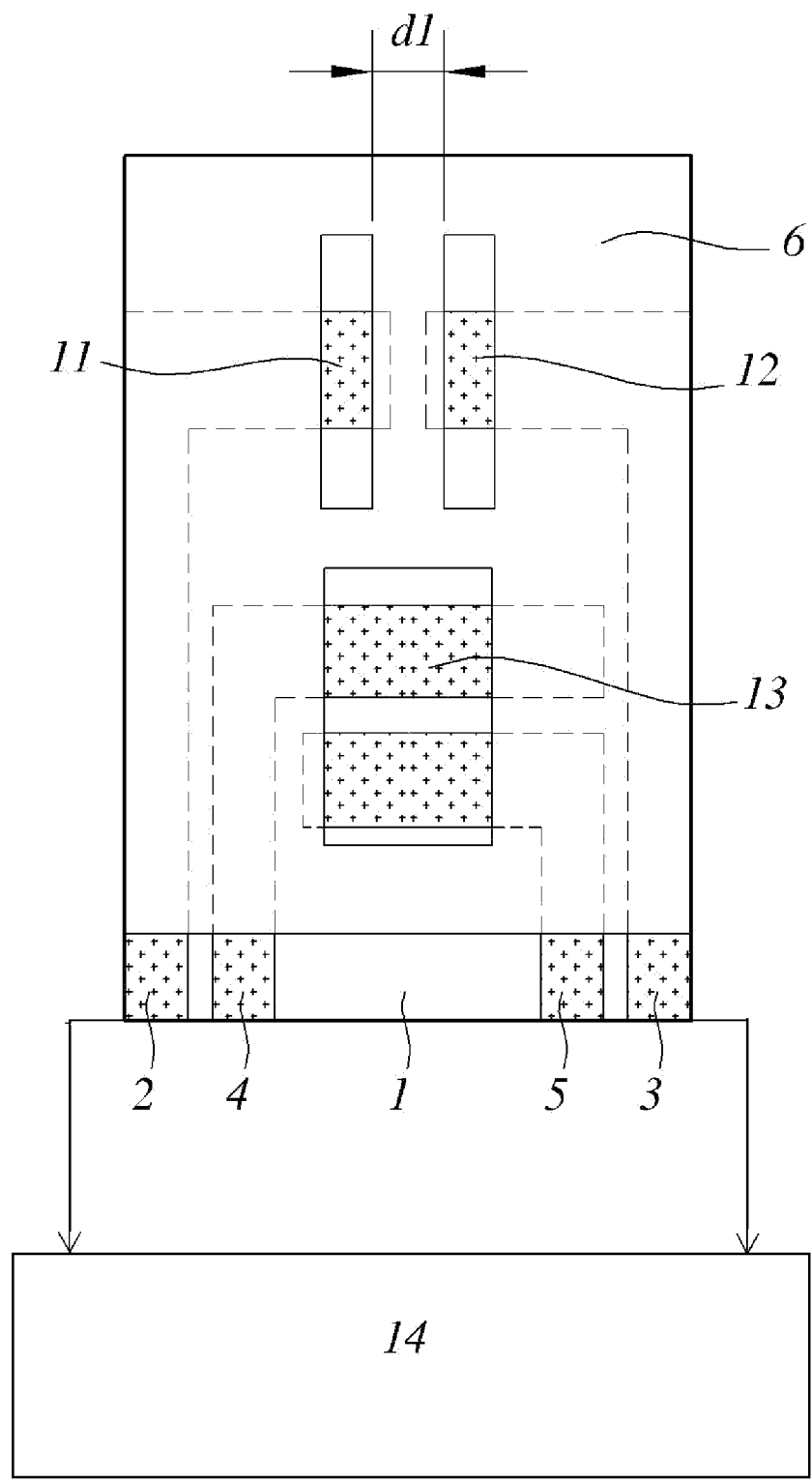
FIG. 2 is an enlarged view of an electrode part in FIG. 1.

The present invention provides an electrochemical biosensor, comprising:
a lower substrate;
a first electrode part including a first working electrode and a first auxiliary electrode which are formed on the lower substrate;
a second electrode part including a second working electrode and a second auxiliary electrode which are formed on the lower substrate;
a reagent layer formed on the second working electrode or the second auxiliary electrode, the reagent layer including an electron transfer mediator;
an insulation cover having regions which correspond to first, second and third reaction units and are partitioned to have cavities, respectively, wherein the first reaction unit is positioned at the first working electrode, a second reaction unit is positioned at the first auxiliary electrode, and a third reaction unit is positioned at the second working electrode;
an intermediate substrate equipped with a microchannel sample cell part to successively guide a blood sample into the first electrode part and the second electrode part; and
an upper substrate,
wherein areas of and a distance between the first working electrode and the first auxiliary electrode exposed at the first reaction unit and the second reaction unit are constant by means of the insulation cover (see FIGS. 1 and 2).

In the biosensor according to the present invention, the lower substrate serves as a board of a biosensor. As a material for the lower substrate, ceramic, a glass plate, or a polymeric material may be used. Preferably, an organic polymeric material such as polyester, polyvinyl chloride, and polycarbonate may be used.

In the biosensor according to the present invention, the first electrode part plays a role in assaying a hematocrit value by measuring electrical conductivity of a blood sample.

Generally, highly accurate measurement of a blood glucose concentration is need for prescription of diabetic patients. An error occurs in a measured glucose concentration value depending on a blood hematocrit value of patients, and thus a process for correcting the error is needed.

Specifically, the first electrode part including a first working electrode and a first auxiliary electrode allows a hematocrit value in a blood sample to be assayed through electrical conductivity measured by applying an alternating current (AC) voltage of 1 kHz or more, and also allows a more accurate blood glucose concentration to be measured by correcting a glucose concentration in the blood sample by use of the measured hematocrit value.

In the biosensor according to the present invention, the second electrode part plays a role in measuring a glucose concentration in a blood sample.

Specifically, the second electrode part includes a second working electrode and a second auxiliary electrode, and measures a glucose concentration in a blood sample by applying a direct current (DC) voltage.

A material of electrodes used for the biosensor according to the present invention may be any conductive material and is not specifically limited. Examples of conductive materials may include silver epoxy, palladium, copper, gold, platinum, iridium, silver/silver chloride, carbon, and modified carbon in which a particular oxidation-reduction pair or other additives are supplemented. The working electrode and auxiliary electrode may be formed by performing screen-printing, physical vapor deposition, or etching process on a conductive material on a board or by attaching a conductive tape.

In the biosensor according to the present invention, the reagent layer including the electron transfer mediator further includes a redox enzyme.

The redox enzyme is reduced through a reaction with glucose to be measured. The reduced enzyme then reacts with an electron transfer mediator thereby quantitating glucose. Examples of the redox enzyme may include flavin adenine dinucleotide-glucose dehydrogenase (FAD-GDH), nicotinamide adenine dinucleotide-glucose dehydrogenase (NAD-GDH), pyrroloquinoline quinone-glucose dehydrogenase (PQQ-GDH), glucose oxidase (GOx), etc.

Further, the electron transfer mediator carries out a redox reaction with the reduced enzyme through a reaction with glucose. The obtained electron transfer mediator in a reduced state plays a role in generating a current on a surface of an electrode to which an oxidation potential is applied.

As the electron transfer mediator, a metal-containing complex, and thionin or a derivative thereof may be mixed and used together; however, the conventionally used compound may also be used, for example, hexaammineruthenium(III) chloride, potassium ferricyanide, potassium ferrocyanide, dimethylferrocene (DMF), ferricinium, ferocene monocarboxylic acid (FCOOH), 7,7,8,8-tetracyanoquinodimethane (TCNQ), tetrathia fulvalene (TTF), nickelocene (Nc), N-methyl acidinium (NMA+), tetrathiatetracene (TTT), N-methylphenazinium (NMP+), hydroquinone, 3-dimethylaminobenzoic acid (MBTHDMAB), 3-methyl-2-benzothiozolinone hydrazone, 2-methoxy-4-allylphenol, 4-aminoantipyrin (AAP), dimethylaniline, 4-aminoantipyrene, 4-methoxynaphthol, 3,3',5,5'-tetramethyl benzidine (TMB), 2,2-azino-di-[3-ethyl-benzthiazoline sulfonate], o-dianisidine, o-toluidine, 2,4-dichlorophenol, 4-amino phenazone, benzidine, prussian blue, bipyridine-osmium complex.

Generally, when assaying a hematocrit value, it is an important factor to make a working electrode and an auxiliary electrode have the same area for the purpose of accurate measurement. However, when an electrode is printed on a biosensor in a mass production, printing is not carried out as exactly as desired depending on constituent materials (e.g., a carbon electrode) and an inclined edge of the electrode tends to slightly flow down. Also, as the printed electrode is getting thicker, an area of the inclined edge of the electrode becomes greater and thus a reaction occurred in an unspecified area increases, thereby resulting in increase in edge effect. It is problematic in that preciseness and reliability of a measured hematocrit value is reduced.

To solve above described problem, as shown in FIGS. 1 and 2, the present invention reduces a measurement error by making the first working electrode and the first auxiliary electrode have substantially constant areas, which are exposed to a blood sample, and maintaining a constant distance therebetween using an insulation cover.

Figure 5:
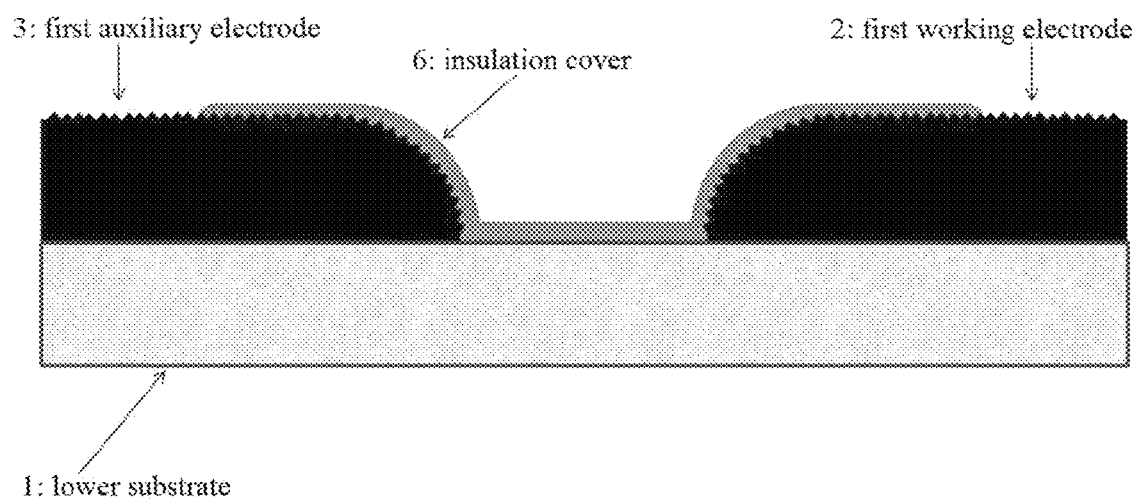
FIG. 5 is an exemplary view illustrating an inclined edge of the first working electrode and the first auxiliary electrode in FIG. 1

More specifically, an error in a measured conductive value caused by the flow-down phenomenon during printing may be minimized by forming an insulation cover having a thickness smaller than a thickness as measured from a top side of the lower substrate to top sides of the first working electrode and the first auxiliary electrode (see FIG. 5).

As a preferred example of forming an insulation cover thinner than the electrode, a printing method with hydrophobic insulation ink may be used. As the hydrophobic insulation ink, polyacryl, epoxy, and ceramic-based hydrophobic ink may be used.

Also, the first reaction unit and the second reaction unit are positioned on a line perpendicular to a longitudinal direction along which blood flows into a microchannel sample cell part such that they are overlapped at least in part, wherein the first reaction unit is positioned at the first working electrode defined by the insulation cover and the second reaction unit is positioned at the first auxiliary electrode.

It is preferable that the first reaction unit positioned at the first working electrode and the second reaction unit positioned at the first auxiliary electrode have the same form (e.g., rectangular, square, circular, and oval forms). Preferably, a rectangular form or a square form is convenient for manufacture.

More preferably, the first reaction unit positioned at the first working electrode and the second reaction unit positioned at the first auxiliary electrode are positioned in a decalcomania form with respect to a central line of a longitudinal direction, on a line perpendicular to a longitudinal direction along which blood flows into a microchannel sample cell part.

Figure 3:
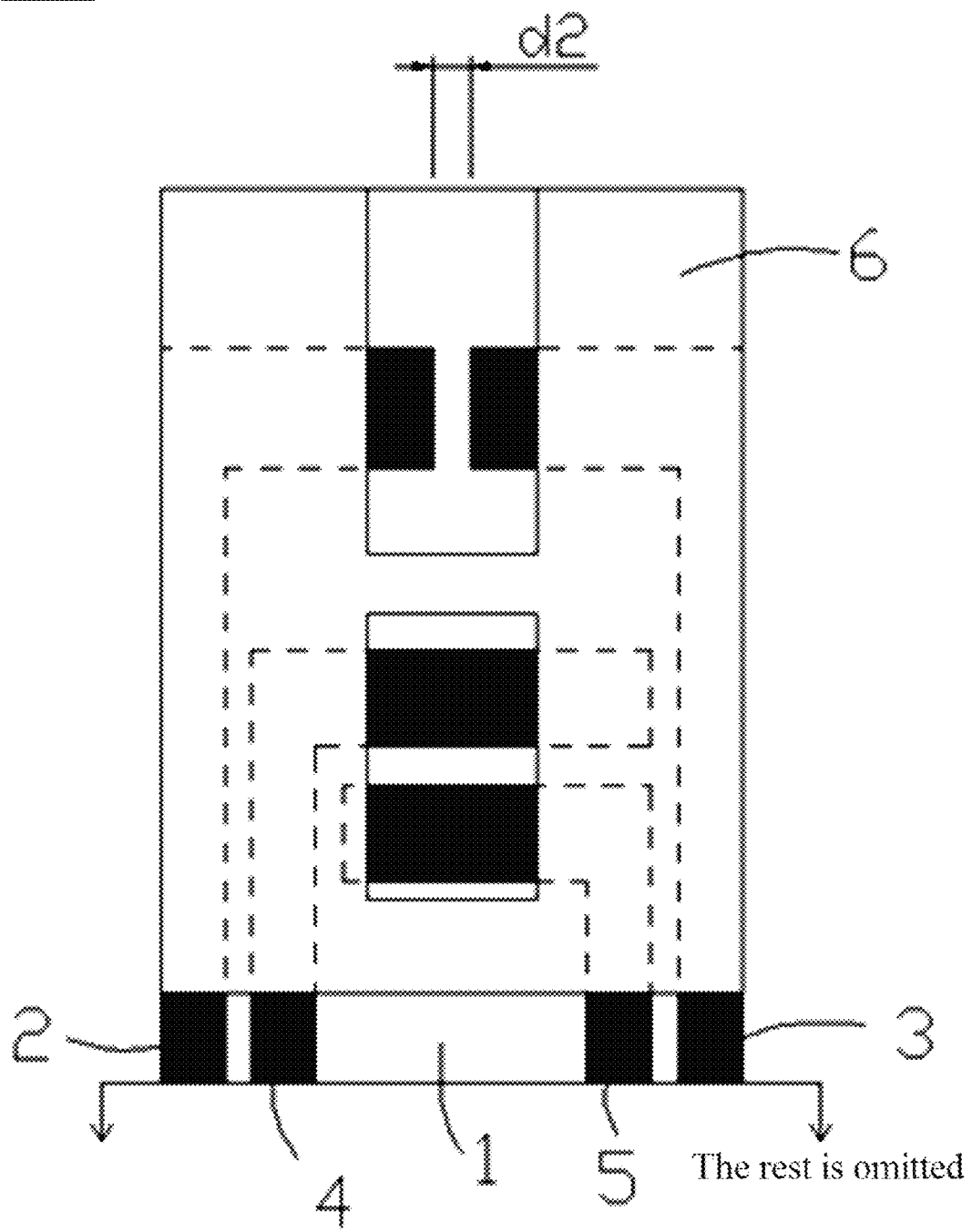
FIG. 3 is an enlarged view of an electrochemical biosensor according to Comparative Example 1 of the present invention, wherein areas of a first working electrode and a first auxiliary electrode, which are exposed to a blood sample, are not defined by an insulation cover.

In the case where no insulation cover is formed between the first working electrode and the first auxiliary electrode, as shown in FIG. 3, a problem arises in which areas of the working electrode and the auxiliary electrode are largely varied.

In the biosensor according to the present invention, the intermediate substrate equipped with a microchannel sample cell part plays a role in successively introducing a blood sample into the first electrode part and the second electrode part and also plays a role in attaching the upper substrate and the lower substrate through an adhesive coated on both sides of the intermediate substrate.

Considering easier introduction of a blood sample, it is preferable that a microchannel having the width of 0.5-2 mm and the height of 50-250 μm is formed in the microchannel sample cell part.

In the electrochemical biosensor according to the present invention, the upper substrate has an air outlet to facilitate introduction of a blood sample through the above-described microchannel sample cell part by means of capillarity and serves as a finishing material of the biosensor.

Further, the present invention provides a method for precisely measuring a blood glucose concentration by applying a hematocrit value using the biosensor, the method comprising:

Also, the present invention provides a method for precisely measuring a blood glucose concentration by applying a hematocrit value using the biosensor, the method comprising:

introducing a blood sample into a microchannel sample cell part (step 1);

calculating a hematocrit value by measuring an electrical conductivity of the blood sample at a first electrode part (step 2);

calculating a glucose concentration by measuring a signal at a second electrode part (step 3); and correcting the glucose concentration calculated at the second electrode part by applying the hematocrit value calculated at the first electrode part (step 4).

Hereinafter, the method according to the present invention will be described in more detail step by step.

In the method according to the present invention, step 1 is a step of introducing a blood sample into a microchannel sample cell part.

A preferable amount of a blood sample used for collecting the blood sample from patients with minimized pain during blood collection is in the range of 0.1 to 0.7 0 μl. The sample is introduced without a pretreatment process. By using the biosensor used in the measuring method of the present invention, blood glucose can be accurately and rapidly measured from the small amount of the blood sample. This is because a microchannel having the width of 0.5-2 mm and the height of 50-250 μm is formed in the microchannel sample cell part of the biosensor to facilitate introduction of a blood sample.

In the method according to the present invention, step 2 is a step of calculating a hematocrit value by measuring electrical conductivity of the blood sample at the first electrode part, and step 3 is a step of calculating a glucose concentration by measuring a signal at the second electrode part.

Specifically, an overall measuring procedure may be controlled by using DC, low-frequency or high-frequency AC, a high-impedance or various types of pulse, and preferably, rectangular wave, triangular wave, semi sinusoidal wave, or gaussian wave between the working electrode and the auxiliary electrode of each of the first and second electrode parts.

As one example, when the biosensor according to the present invention is inserted into a measuring device thereof, a certain predetermined AC voltage is applied between the working electrode and the auxiliary electrode of the first and/or second electrode part(s). Voltages applied to the working electrode and the auxiliary electrode are independent, and a whole circuit forms an open circuit. An electrical change resulted from introduction of the sample appears as an electrical potential difference in an open circuit state. An electrical potential difference signal is used as a start signal for a measuring process of the biosensor.

It is preferable that the reagent layer including an electron transfer mediator is formed either on the second working electrode or the second auxiliary electrode, and the electrodes are arranged such that they are spaced apart from each other by 20 µm to 2 mm, more preferably by 80 µm to 0.5 mm. Moreover, the reagent layer may further include a redox enzyme, and also additionally include fatty acid and quaternary ammonium.

Herein, it is possible to use, as the redox enzyme, flavin adenine dinucleotide-glucose dehydrogenase (FAD-GDH), nicotinamide adenine dinucleotide-glucose dehydrogenase (NAD-GDH), pyrroloquinoline quinone-glucose dehydrogenase (PQQ-GDH), glucose oxidase (GOx) and so forth.

As the electron transfer mediator, a metal-containing complex, and thionin or a derivative thereof may be mixed and used together; however, the conventionally used compound also may also be used, for example, hexaammineruthenium(III) chloride, potassium ferricyanide, potassium ferrocyanide, dimethylferrocene (DMF), ferricinium, ferocene monocarboxylic acid (FCOOH), 7,7,8,8-tetracyanoquino-dimethane (TCNQ), tetrathia fulvalene (TTF), nickelocene (Nc), N-methyl acidinium (NMA+), tetrathiatetracene (TTT), N-methylphenazinium (NMP+), hydroquinone, 3-dimethylaminobenzoic acid (MBTH-DMAB), 3-methyl-2-benzothiozolinone hydrazone, 2-methoxy-4-allylphenol, 4-aminoantipyrin (AAP), dimethylaniline, 4-aminoantipyrene, 4-methoxynaphthol, 3,3',5,5'-tetramethyl benzidine (TMB), 2,2-azino-di-[3-ethyl-benzthiazoline sulfonate], o-dianisidine, o-toluidine, 2,4-dichlorophenol, 4-amino phenazone, benzidine, prussian blue, bipyridine-osmium complex.

In the method according to the present invention, step 4 is a step of correcting the glucose concentration calculated at the second electrode part by applying the hematocrit value calculated at the first electrode part. Measuring order of the first and second electrode parts is not limited.

Specifically, hematocrit is measured through a correction equation of hematocrit, which is previously inputted in a measuring device, by using a conductivity value measured at the first electrode part. Then, an accurate measured value is obtained by calculating the blood glucose value measured at the second electrode part into a corrected value in which influence of hematocrit is reflected by using each hematocrit correction equation previously inputted.

As described above, according to the present invention, an electrochemical biosensor including a first electrode part for correcting a measured hematocrit value and a second electrode part for measuring a glucose concentration is effective in improving accuracy of a measured hematocrit value and in more improving accuracy of a measured blood glucose concentration using the measured hematocrit values for correction, because an insulation cover is made thinner than a working electrode and an auxiliary electrode, so that areas of a first working electrode and a first auxiliary electrode of the first electrode part exposed to a blood sample become equal; a distance between the first working electrode and the second working electrode becomes constant; and electrode areas are maintained constantly by the insulation cover even when a positioning error occurs during printing.

MODE FOR CARRYING OUT THE INVENTION

Hereinafter, the present invention will be described in more detail with reference to following examples. However, following examples are illustrative purpose only, and not intended to limit the content of the present invention.

<Example 1> Production 1 of Planar Biosensor in which Areas of Working Electrode and Auxiliary Electrode for Measuring Hematocrit are Defined Constantly by Insulation Cover As illustrated in FIG. 1, a planar biosensor having a cell introducing part with an introduction amount of 0.5 µl as a mean value was produced as an example of a planar biosensor. The planar biosensor was produced with reference to methods published in Korean Patent Application No. 10-2003-0036804, Korean Patent Application No. 10-2005-0010720, Korean Patent Application No. 10-2007-0020447, Korean Patent Application No. 10-2007-0021086, Korean Patent Application No. 10-2007-0025106, Korean Patent Application No. 10-2007-0030346, and E. K. Bauman et al., *Analytical Chemistry*, vol 37, p 1378, 1965; K. B. Oldham in "Microelectrodes: Theory and Applications," Kluwer *Academic Publishers*, 1991., etc.

In FIG. 1,

1 is a lower substrate made of polyester on which a working electrode and an auxiliary electrode are formed;

2 to 5 are electrodes produced by screen-printing carbon/graphite, (where 2 is a first working electrode, 3 is a first auxiliary electrode, 4 is a second working electrode, and 5 is a second auxiliary electrode);

11 is a first reaction unit positioned at the first working electrode, 12 is a second reaction unit positioned at the first auxiliary electrode, and 13 is a third reaction unit positioned at the second working electrode and the second auxiliary electrode.

6 is an insulation cover which defines a first electrode part and a second electrode part, and defines areas of the first working electrode and the first auxiliary electrode identically;

7 is a reagent layer including a redox enzyme and an electron transfer mediator;

8 is an intermediate substrate which has the thickness of 0.10 mm and is provided with a microchannel sample cell part to guide a blood sample to be successively introduced into the first electrode part and the second electrode part, wherein the intermediate substrate plays a role in attaching the lower substrate and an upper substrate through an adhesive coated on both sides thereof;

9 is the upper substrate which is made of polyester and provided with an air outlet for allowing blood to be infiltrated into the microchannel sample cell part; and

10 is the air outlet. 14 represents a measuring device electrically connected to the first and/or second working and auxiliary electrodes.

<Comparative Example 1> Production 1 of Planar Biosensor in Which Areas of Working Electrode and Auxiliary Electrode for Measuring Hematocrit are not Defined As illustrated in FIG. 3, a biosensor was produced by the same method as in Example 1, in which an insulation cover 6 is not disposed between a first working electrode and a second working electrode.

Figure 4:
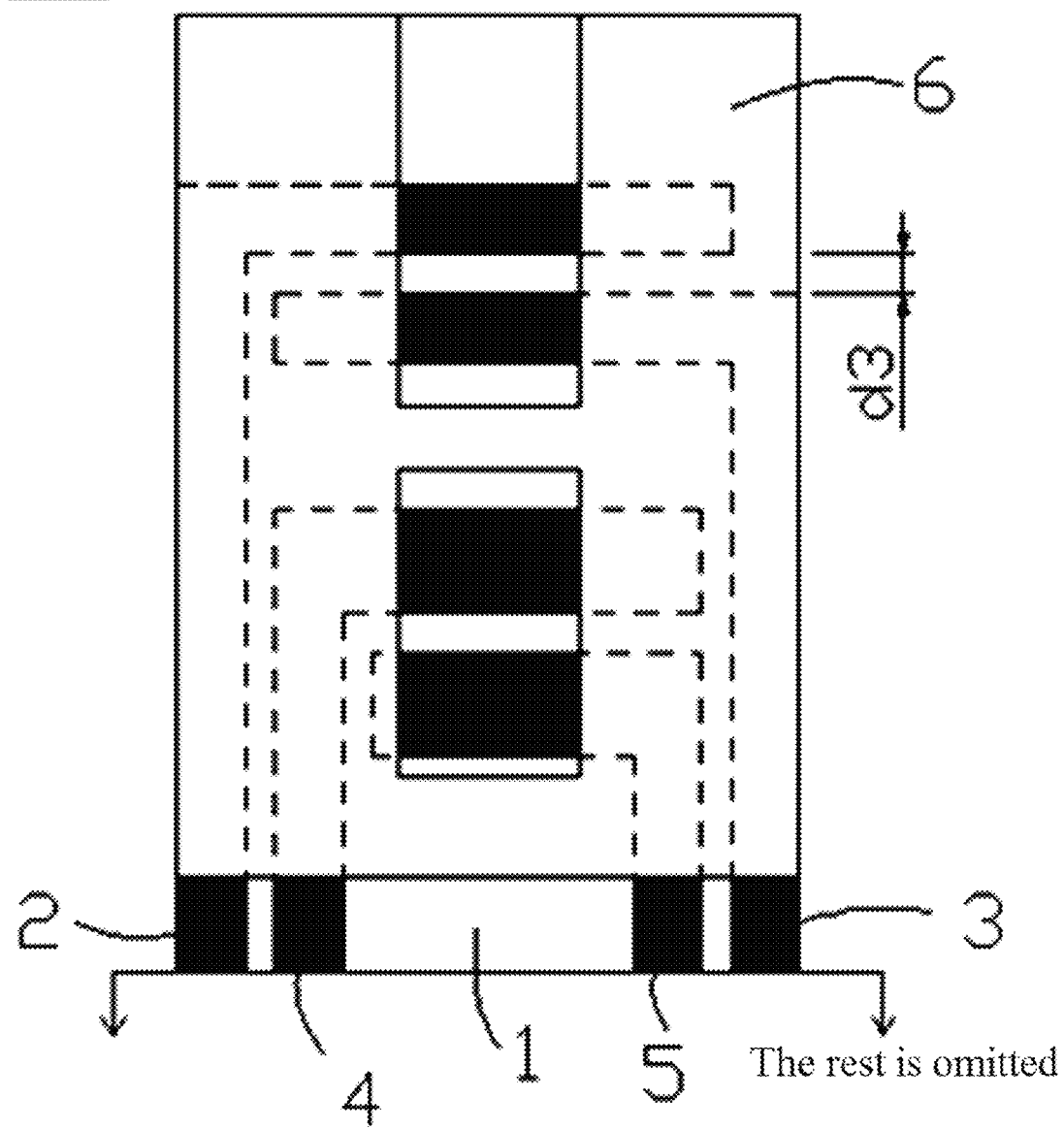
FIG. 4 is an enlarged view of a planar sensor showing an electrochemical biosensor according to Comparative Example 2 of the present invention in which a first working electrode and a first auxiliary electrode exposed to a blood sample are successively positioned with respect to a blood inflow direction.

<Comparative Example 2> Production 2 of Planar Biosensor in Which Areas of Working Electrode and Auxiliary Electrode for Measuring Hematocrit are not Defined As illustrated in FIG. 4, a biosensor was produced by the same method as in Example 1, in which an insulation cover 6 is provided such that first and second working electrodes are successively positioned with respect to a direction of a blood inflow direction and these electrodes are not defined by the insulation cover.

<Experimental Example 1> Conductivity Measurement for Hematocrit

To investigate accuracy of hematocrit measurement of the biosensors produced in Example 1 and Comparative Examples 1 and 2, an experiment was performed as follows.

Specifically, 81 mV of peak-to-peak voltage with the AC frequency of 2.5 kHz was applied to a first electrode part, and conductivity of blood prepared to have hematocrit of 0, 10, 20 30, 40, 50, 60 and 70% was measured five times. The results were shown in table 1 below and FIGS. 8 to 10.

TABLE 1

|  | Example 1 | Comparative Example 1 | Comparative Example 2 |
|---|---|---|---|
| Mean standard deviation ($\overline{SD}$) | 0.00056 | 0.00291 | 0.00251 |
| Slope ($S_G$) | −0.00080 | −0.00110 | −0.00120 |
| $\overline{SD}/S_G$ | −0.703 | −2.648 | −2.094 |

FIG. 8 is a graph showing the measured results of electrical conductivity versus hematocrit by using the sensor produced in Example 1 (where, "% Hct" means % hematocrit).

FIG. 9 is a graph showing the measured results of electrical conductivity versus hematocrit by using the sensor produced in Comparative Example 1 (where, "% Hct" means % hematocrit).

FIG. 10 is a graph showing the measured results of electrical conductivity versus hematocrit by using the sensor produced in Comparative Example 2 (where, "% Hct" means % hematocrit).

As shown in FIGS. 8 to 10, a slope of conductivity per % hematocrit was measured as '−0.0008' in Example 1, and '−0.0011' in Comparative Example 1, since a distance (d1) between the first working electrode and the second working electrode is longer than a distance (d2) in Comparative Example 1 (see equation (1) in the Background Art section).

As shown in table 1, a value obtained by dividing a mean standard deviation by a slope [$\overline{SD}/SG$] is '−0.703' in Example 1 and '−2.648' in Comparative Example 1. Thus, it can be found that the biosensor in Example 1 shows more precise performance by approximately 3.8 times [=(−2.648)/(−0.703)]. Further, a value obtained by dividing a mean standard deviation by a slope [$\overline{SD}/SG$] is '−2.094' in Comparative Example 2. Thus, it can be found that the biosensor in Example 1 shows more precise performance by approximately 4.1 times [=(−2.904)/(−0.703)]. In addition, the structure of Comparative Example 2 is undesirable in terms of users' convenience because an amount of blood needed for measurement increases.

Figure 6:
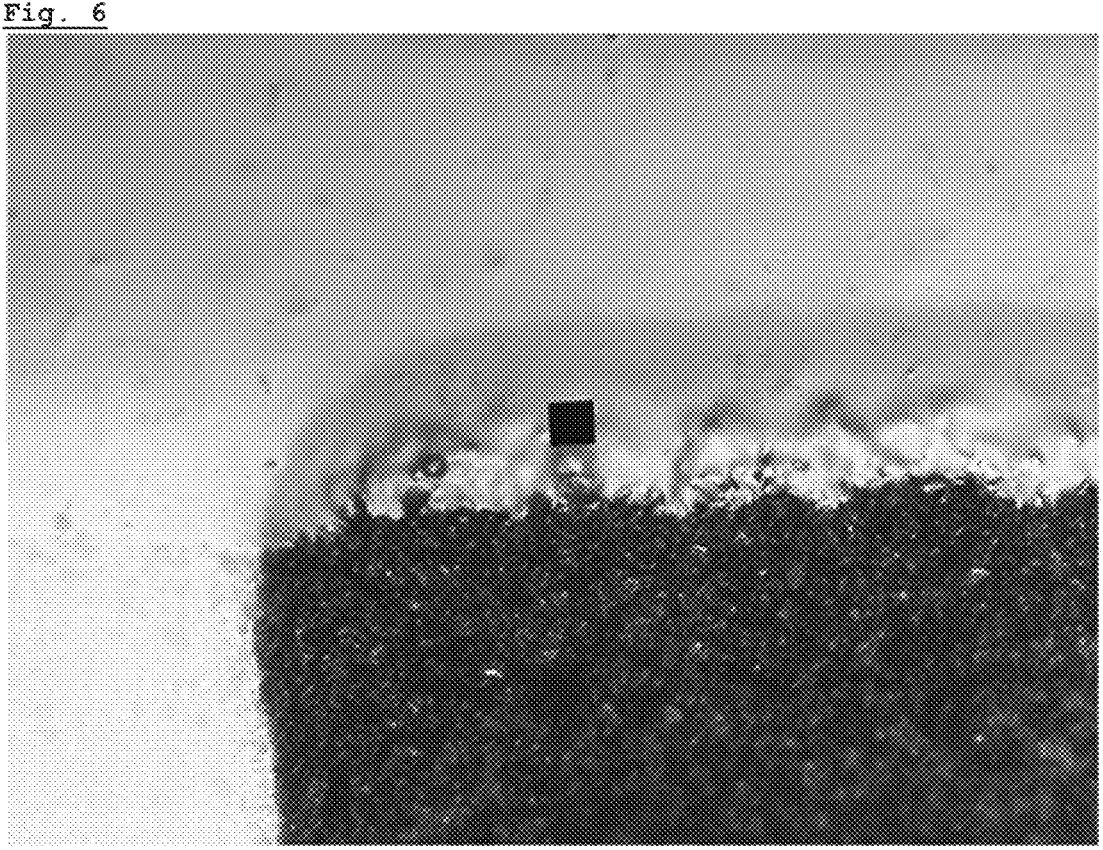
FIG. 6 is a microscopic image showing a part of the electrode which is defined by the insulation cover as in FIG. 2.
Figure 7:
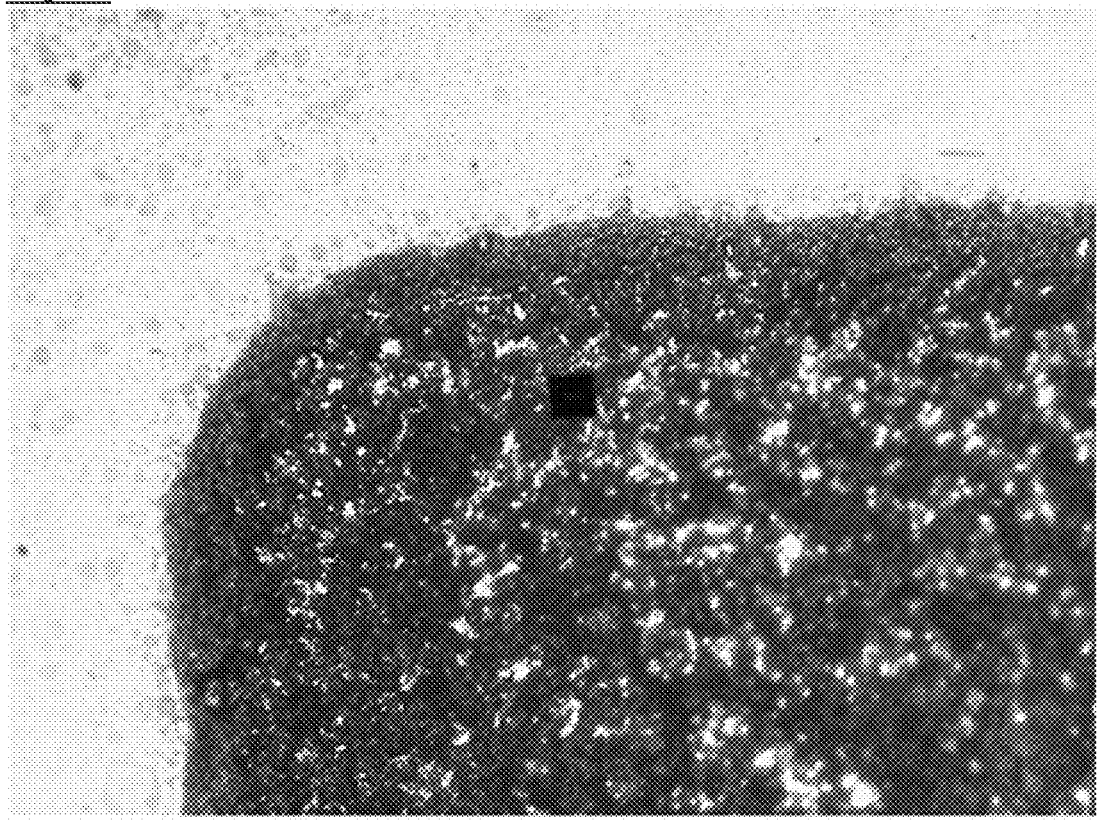
FIG. 7 is a microscopic image showing a part of the electrode which is not defined by the insulation cover as in FIG. 3

These results, as shown in FIG. 5, showed that the insulation cover according to the present invention has a thickness two or more times thinner than that of a carbon/graphite electrode and is thus effective in defining an area more accurately. Also, as shown in FIG. 7, it can be found that an inclined edge of a printed carbon/graphite electrode is round to make it difficult to delicately define areas while an inclined edge of a carbon/graphite electrode onto which an insulation cover is printed as shown in FIG. 6 can be defined to have approximately a right angle.

Therefore, since the electrochemical biosensor according to the present invention has an effect of significantly improving measurement accuracy by constantly maintaining areas of and a distance between a first working electrode and a first auxiliary electrode exposed at first and second reaction units as much as possible by virtue of an insulation cover, the present invention is useful as an electrochemical biosensor.

INDUSTRIAL APPLICABILITY

As described above, according to the present invention, an electrochemical biosensor including a first electrode part for correcting a measured hematocrit value and a second electrode part for measuring a glucose concentration is effective in improving accuracy of a measured hematocrit value and in more improving accuracy of a measured blood glucose concentration using the measured hematocrit values for correction, because an insulation cover is made thinner than a working electrode and an auxiliary electrode, so that areas of a first working electrode and a first auxiliary electrode of the first electrode part exposed to a blood sample become equal; a distance between the first working electrode and the second working electrode becomes constant; and electrode areas are maintained constantly by the insulation cover even when a positioning error occurs during printing.

The invention claimed is:

1. An electrochemical biosensor, comprising:
   a lower substrate;
   a first electrode part comprising a first working electrode and a first auxiliary electrode which are formed on the lower substrate;
   a second electrode part comprising a second working electrode and a second auxiliary electrode which are formed on the lower substrate;
   a reagent layer formed on the second working electrode or the second auxiliary electrode, the reagent layer including an electron transfer mediator;
   an insulation cover having regions which correspond to first, second and third reaction units and are partitioned to have cavities, respectively, wherein the first reaction unit is positioned at the first working electrode, a second reaction unit is positioned at the first auxiliary electrode, and a third reaction unit is positioned at the second working electrode;
   an intermediate substrate equipped with a microchannel sample cell part to successively guide a blood sample into the first electrode part and the second electrode part; and
   an upper substrate,
      wherein the first electrode part is able to be electrically connected to a measuring device used in calculating hematocrit by measuring conductivity of a blood sample at the first electrode part, and wherein the first working electrode is devoid of a reagent layer thereon, and
      wherein the first reaction unit positioned at the first working electrode and the second reaction unit positioned at the first auxiliary electrode are each positioned, at least in part, on an imaginary line perpendicular to a longitudinal direction along which blood flows into the microchannel sample cell part.

2. The electrochemical biosensor as set forth in claim 1, wherein the insulation cover covers at least one inclined edge of the first working electrode exposed at the first reaction unit, and at least one inclined edge of the first auxiliary electrode exposed at the second reaction unit.

3. The electrochemical biosensor as set forth in claim 1, wherein a thickness of the insulation cover is smaller than a thickness of the electrode.

4. The electrochemical biosensor as set forth in claim 1, wherein the insulation cover is printed with a hydrophobic insulation ink.

5. The electrochemical biosensor as set forth in claim 4, wherein the hydrophobic insulation ink is one selected from the group consisting of polyacryl-based, epoxy-based and ceramic-based inks.

6. The electrochemical biosensor as set forth in claim 1, wherein the first reaction unit positioned at the first working electrode and the second reaction unit positioned at the first auxiliary unit have the same shape.

7. The electrochemical biosensor as set forth in claim 1, wherein the first reaction unit positioned at the first working electrode and the second reaction unit positioned at the first auxiliary unit are positioned in a decalcomania form with respect to a central line of a longitudinal direction, on a line perpendicular to a longitudinal direction along which blood flows into the microchannel sample cell part.

8. The electrochemical biosensor as set forth in claim 1, wherein the reagent layer further includes a redox enzyme.

9. The electrochemical biosensor as set forth in claim 1, wherein a current caused by a redox reaction of glucose in a blood sample is able to be measured at the second electrode part.

10. The electrochemical biosensor as set forth in claim 1, wherein an alternating current (AC) voltage is able to be applied at the first electrode part so as to measure electrical conductivity.

11. The electrochemical biosensor as set forth in claim 1, wherein the second electrode part measures a current caused by a redox reaction of glucose by applying a direct current (DC) voltage.

12. A method for precisely measuring a blood glucose concentration using the electrochemical biosensor of claim 1,
wherein the method comprises the steps of:
inserting the electrochemical biosensor of claim 1 into a measuring device;
introducing a blood sample into the microchannel sample cell part;
measuring an electrical conductivity of the blood sample at the first electrode part and calculating a hematocrit value using the measuring device and a predetermined equation between hematocrit value and the measured electrical conductivity;
calculating a glucose concentration using the measuring device by measuring a signal at a second electrode part; and
correcting the glucose concentration calculated at the second electrode part by applying the hematocrit value calculated at the first electrode part.

13. The method according to claim 12, wherein the electrical conductivity is measured by applying a predetermined potential between the first working electrode and the first auxiliary electrode.

14. The method according to claim 12, wherein said correcting is conducted using a predetermined equation between a hematocrit value and a calculated glucose concentration.

* * * * *